United States Patent [19]

Morgan

[11] Patent Number: 5,192,676
[45] Date of Patent: Mar. 9, 1993

[54] TYPE II RESTRICTION ENDONUCLEASE, ASCI, OBTAINABLE FROM ARTHROBACTER SPECIES AND A PROCESS FOR PRODUCING THE SAME

[75] Inventor: Richard D. Morgan, Middleton, Mass.

[73] Assignee: New England Biolabs, Inc., Beverly, Mass.

[21] Appl. No.: 650,802

[22] Filed: Feb. 5, 1991

[51] Int. Cl.⁵ ............................................. C12N 9/22
[52] U.S. Cl. ................................... 435/199; 435/830
[58] Field of Search .................. 435/199, 172.3, 830

[56] References Cited

U.S. PATENT DOCUMENTS

| | | | |
|---|---|---|---|
| 4,983,522 | 1/1991 | Barsomian | 435/172.3 |
| 4,983,542 | 1/1991 | VanCott et al. | 435/172.3 |
| 4,987,074 | 1/1991 | Lunnen et al. | 435/172.3 |
| 4,988,620 | 1/1991 | VanCott et al. | 435/199 |
| 4,996,151 | 2/1991 | Brooks et al. | 435/172.3 |
| 4,999,293 | 3/1991 | Barsomian et al. | 435/172.3 |
| 4,999,294 | 3/1991 | Looney et al. | 435/172.3 |
| 5,002,882 | 3/1991 | Lunnen et al. | 435/172.3 |
| 5,004,691 | 4/1991 | Chen et al. | 435/172.3 |
| 5,015,581 | 5/1991 | Benner et al. | 435/172.3 |
| 5,030,569 | 7/1991 | Lunnen et al. | 435/172.3 |
| 5,053,330 | 10/1991 | Lunnen et al. | 435/172.3 |

FOREIGN PATENT DOCUMENTS 076696 4/1983 European Pat. Off. .
193413 9/1986 European Pat. Off. .

OTHER PUBLICATIONS

Kessler, C., et al. (1990) Gene 92, 1,134,135.
Endow, J. Mol. Biol. 112:521 (1977).
Waalwijk, Nucleic Acids Res. 5:3231 (1978).
Gingeras, Proc. Natl. Acad. Sci. 80:402 (1983).
Lunnen, Gene 74:25-32 (1988).
Sauser, F. PNAS 74:5463-5467 (1977).
Brown, N. L. J. Mol. Biol. 140, 143-148 (1980).

*Primary Examiner*—Charles L. Patterson, Jr.
*Attorney, Agent, or Firm*—Gregory D. Williams; David G. Conlin

[57] ABSTRACT

The present invention provides a novel type II restriction endonuclease obtainable from Arthrobacter species. The endonuclease known as Asc I, recognizes the following nucleotide sequence and has a cleavage point indicated by the arrows:

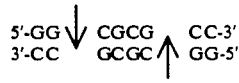

Also described is a process for obtaining Asc I from Arthrobacter species.

5 Claims, 1 Drawing Sheet

FIG. 1 DETERMINATION OF THE ASC I CLEAVAGE SITE
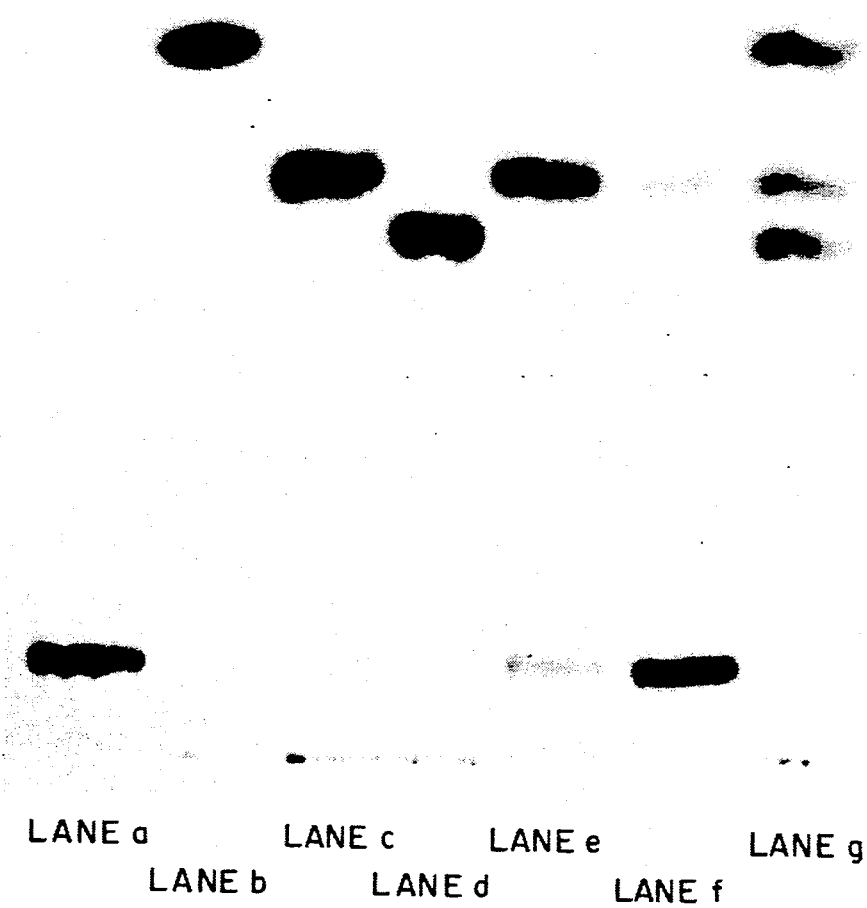
LANE a  LANE c  LANE e  LANE g
  LANE b  LANE d  LANE f

TYPE II RESTRICTION ENDONUCLEASE, ASCI, OBTAINABLE FROM ARTHROBACTER SPECIES AND A PROCESS FOR PRODUCING THE SAME

BACKGROUND OF THE INVENTION

The present invention relates to a new Type II restriction endonuclease, Asc I, obtainable from Arthrobacter species, and to the process for producing the same.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed. Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriction endonucleases have degenerate or relaxed specificities in that they recognize multiple bases at one or more positions in their recognition sequence, and some restriction endonucleases recognize asymmetric sequences. Hae III, which recognizes the sequence GGCC, is an example of a restriction endonuclease having a symmetrical, non-degenerate recognition sequence, while Hae II, which recognizes (Pu)GCGC(Py) typifies restriction endonucleases having a degenerate or relaxed recognition sequence. Endonucleases with symmetrical recognition sequences generally cleave symmetrically within or adjacent to the recognition site, while those that recognize asymmetric sequences tend to cleave at a distance of from 1 to 18 nucleotides away from the recognition site. Over one hundred twenty-five unique restriction endonucleases have been identified among several thousands of bacterial species that have been examined to date.

Bacteria usually possess only a small number of restriction endonucleases per species. The endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT), PuGCGCPy and GGCC respectively *Escherichia coli* RY13, on the other hand, synthesizes only one enzyme, EcoRI, which recognizes the sequence GAATTC.

While not wishing to be bound by theory, it is thought that in nature restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecules and cleaving them in each place that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

More than 1,000 restriction endonucleases have been isolated from bacterial strains. Of these, about 125 recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., *J. Mol. Biol.* 112:521 (1977); Waalwijk, et al., *Nucleic Acids Res.* 5:3231 (1978)) and in cleavage rate at various sites (XhoI v. PaeR7I, Gingeras, et al., *Proc. Natl. Acad. Sci.* U.S.A. 80:402 (1983)).

There is a continuing need for novel type II restriction endonucleases. Although type II restriction endonucleases which recognize a number of specific nucleotide sequences are currently available, new restriction endonucleases which recognize novel sequences provide greater opportunities and ability for genetic manipulation. In particular, there are few endonucleases available which recognize eight specific nucleotides. These include NotI (GCGGCCGC), SfiI (GGCCNNNNNGGCC), PacI (TTAATTAA), Sse83-87I (CCTGCAGG), and FseI (GGCCGGCC), although FseI is not commercially available. Type II restriction endonucleases which recognize eight nucleotides are particularly useful in the manipulation of very large DNA molecules, such as whole chromosomes, because the requirement of eight specified nucleotides for cleavage means that these enzymes cleave less frequently and produce a fewer, more managable number of fragments from a given DNA molecule. Each new unique endonuclease enables scientists to precisely cleave DNA in new places, with all the opportunities this offers.

SUMMARY OF THE INVENTION

In accordance with the present invention, there is provided a novel restriction endonuclease obtainable from Arthrobacter species, hereinafter referred to as "AscI", which endonuclease:

(1) recognizes the nucleotide sequence GGCGCGCC in a double-stranded DNA molecule as shown below,

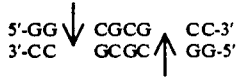

(wherein G represents guanine and C represents cytosine);
(2) cleaves said sequence in the phosphodiester bonds between the 2nd-most 5' G and the 5'-most C as indicated with the arrows; and
(3) cleaves double-stranded lambda c1857 DNA at positions 3521 and 16648, cleaves Adeno2 DNA at positions 15665 and 25337, and does not cleave pUC19, pBR322, phiX174, SV40, M13mp18 and phage T7 DNAs The present invention further relates to a process for the production of the novel restriction endonuclease AscI, which process comprises culturing Arthrobacter species under conditions suitable for expressing AscI, collecting the cultured cells, obtaining a cell-free extract therefrom and separating and collecting the restriction endonuclease AscI from the cell-free extract.

BRIEF DESCRIPTION OF THE FIGURES

FIG. 1—This is a autoradiogram of a thin layer chromatogram used to determine the AscI cleavage site.

DETAILED DESCRIPTION OF THE INVENTION

In accordance with the present invention, AscI is obtained by culturing Arthrobacter species strain NEB#688 and recovering the endonuclease from the cells. A sample of Arthrobacter species NEB#688 has been deposited at the American Type Culture Collection (ATCC) on Dec. 21, 1990 and bears the accession number 55134.

For recovering the enzyme of the present invention A. species may be grown using any suitable technique. For example, A. species may be grown in a media comprised of 10 g/L tryptone, 5 g/L yeast extract, 10 g/L NaCl, 1 g/L dextrose, 1 g/L MgC12.6H2O (pH 7.2), which is incubated at 30° C. with agitation and aeration. Cells in the late logarithmic stage of growth are collected by centrifugation and either disrupted immediately or stored frozen at −70° C.

The AscI enzyme can be isolated from A. species cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing AscI. The AscI endonuclease is then purified from the cell-free extract by ion-exchange chromatography, affinity chromatography, molecular sieve chromatography, or a combination of these methods to produce the endonuclease of the present invention.

The endonuclease of the present invention along with its corresponding methylase may also be obtained using recombinant DNA techniques, such as the methylation selection technique disclosed by Wilson, et al., EPO Publication No. 019413, the disclosure of which is herein incorporated by reference. As an example, DNA from a bacterial strain which contains an R-M system, such as A. species, is purified, partially digested with cloning endonucleases, and ligated to an appropriate cleaved, dephosphorylated cloning vector. The ligated DNA is transformed into an appropriate host, such as *E. coli*, the transformants are pooled and the population of cloning vectors are purified to form libraries. The library of clones is then challenged by digesting with an endonuclease which will selectively destroy vectors which do not contain and express the methylase of the R-M system being cloned. Vectors which contain and express the methylase gene of interest will be modified at the endonuclease recognition sites and thus immune from cleavage. The challenged clone pools are then transformed back into the appropriate host to recover the undigested clones. The transformants may be screened for endonuclease activity or cycled through further rounds of purification and selection. Finally, individual transformants are selected and their DNA purified. These clones are analyzed for resistance to cleavage by the endonuclease of interest and for common insert DNA. Cell extracts prepared from transformants which demonstrate endonuclease resistance are assayed in vitro for methyltransferase and endonuclease activities.

A number of R-M systems have proved recalcitrant to cloning by the standard methylase selection method. These systems require modifications to the above approach. See Lunnen, et al., Gene 74:25-32 (1988), the disclosure of which is hereby incorporated by reference herein. For example, the endonuclease(s) used to form libraries may cleave in either or both of the R-M genes. In some systems the methylase and endonuclease genes may not be linked. In other systems, such as BamHI and DdeI, the methylase may not sufficiently protect against cleavage by the corresponding endonuclease, either because of inefficient expression of the methylase in the transformation host, because of the inherent control mechanism for expression of the methylase, or for unknown reasons. Another potential difficulty is that certain methylation patterns may be restricted in some hosts by endogenous host restriction systems, such as McrA, McrB or mrr, resulting in destruction of methylase clones. Another potential problem arises if the endonuclease sought to be cloned is not available in sufficient quantity or purity for methylase selection. Finally, in many systems difficulties are encountered in expressing the endonuclease gene in a host from a different bacterial genus.

The recognition sequence of the endonuclease of the present invention may be determined by mapping the locations of AscI cleavage in various DNAs and comparing the DNA sequences of these regions for homology. The endonuclease of the present invention AscI, was found to cleave lambda phage c1857 DNA in two places. These cut sites were mapped to approximate positions of 3525 and 16650 by simultaneously digesting lambda c1857 DNA with AscI and with endonucleases which cleave at known positions, such as ApaI, SnaBI, XbaI, XhoI, NheI, HindIII, BstEII, Eco0109I, EagI and KpnI. AscI was also found to cleave Adeno2 DNA in two places, which were similarly mapped to approximately 15670 and 25350. The sequence GGCGCGCC was found to occur in lambda at 3521 and 16648 and in Adeno2 at 15665 and 25337, and to occur only in these positions The sequence GGCGCGCC does not occur in pUC19, pBR322, phiX174, M13mp18, SV40 and phage T7 DNAs and these DNAs are not cleaved by AscI. From this evidence it was concluded that AscI recognizes the sequence GGCGCGCC.

An oligonucleotide containing the AscI recognition sequence, AGGCGCGCCT, was synthesized. AscI cleaved this oligonucleotide. This oligonucleotide was inserted by standard techniques into pUC19 DNA (ATCC#37254) at the HincII site to form plasmid pklASCI-1. AscI was found to cleave the pklASCI-1 DNA but not the initial pUC19 plasmid. pklASCI-1 was used to determine the location of cleavage within the recognition sequence, as was cleavage of the linker alone, and the cleavage results confirmed that AscI recognizes the sequence GGCGCGCC.

The point of cleavage within the AscI recognition sequence may be determined through dideoxy sequencing analysis of the terminal base sequence obtained from AscI cleavage of pklASCI-1 (Sanger, F. et al., PNAS 74:5463–5467 (1977), Brown, N. L., et al., J. Mol. Biol. 140, 143–148 (1980)), or by analysis of the products from AscI cleavage of a labeled oligonucleotide which contains the AscI recognition sequence. By the above referenced methods (exemplified in example II) is was found that AscI cleaves the phosphodiester bond between the second-most 5' G and the 5'-most C. in the recognition sequence GG/CGCGCC to produce a 4 base 5' single-stranded extension, as indicated by the arrows:

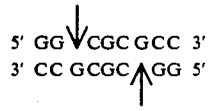

The enzyme of the present invention also has the following properties:

(a) Optimal buffer composition: The optimal buffer tested was 50 mM potassium acetate, 20 mM Trisacetate, 10 mM magnesium acetate, 1 mM dithiothreitol (pH 7.9 at 25° C.). Relative activity in a buffer composed of 10 mM Tris-HCl, 10 mM MgCl2, 50 mM NaCl, 1 mM DTT (pH 7.9@25° C.) or 50 mM Tris-HCl, 10 mM MgCl2, 100 mM NaCl, 1 mM DTT (pH 7.9@25° C.) was 25% and less than 5% in a buffer composed of 10 mM Bis Tris Propane-HCl, 10 mM MgCl2, 1 mM DTT (pH 7.0@25° C.).

(b) Heat Inactivation: 2.5 units of Asc I can be inactivated in twenty minutes at 65° C.

(c) Enzyme Stability: 0.13 units of Asc I cleaves 1 ug Lambda phage DNA mixed with 50 uls 50 mM potassium acetate, 20 mM Tris-acetate, 10 mM magnesium acetate, 1 mM dithiothreitol (pH 7.9 at 25° C.) to completion in sixteen hours at 37° C.

The following examples are given to illustrate embodiments of the present invention as it is presently preferred to practice. It will be understood that the examples are illustrative, and that the invention is not to be considered as restricted except as indicated in the appended claims.

EXAMPLE I

Production of AscI Endonuclease

Arthrobacter species strain NEB 688 (ATCC#55134 was grown in media consisting of 10 g/l tryptone, 5 g/l yeast extract, 10 g/l NaCl, 1 g/l magnesium chloride hexahydrate, 1 g/l glucose (adjusted to pH 7.2). The cells were incubated at 30° C. until late logarithmic stage with aeration and agitation. The cells were harvested by centrifugation and stored frozen at −70° C.

322 g of the cells obtained above were suspended in two volumes buffer A (20 mM Tris-HCl, 0.1 mM EDTA, 6 mM 2-Mercaptoethanol, pH 7.9) adjusted to 0.3 M NaCl. Lysozyme was added to 0.2 mg/ml and the solution was mechanically stirred at 4° C. for 16 hrs. The cell suspension was passed 4 times through a Gaulin press at 11,000 PSI. Approximately 12.3 mg of protein/g cell was released. The lysate was centrifuged at 4° C. for 40 minutes (Sharpless). The supernatant volume was 800 ml at pH 6.6. The debris weight was 130 g. The supernatant contained 400,000 units of Asc I activity.

The supernatant solution was loaded onto a DEAE-Sepharose column (314 ml, equilibrated in buffer A adjusted to 0.3 M NaCl). The flow through was batch collected. The DEAE flow through contained 400,000 units of Asc I activity in 800 mls.

To the flow through was added 1,600 ml of buffer B (20 mM Tris-HCl, 0.1 mM EDTA, 6 mM 2-Mercaptoethanol, pH 7.5). This solution was applied to a 150 ml Heparin-Sepharose column equilibrated in buffer B adjusted to 0.1 M NaCl. The column was washed with 300 mls buffer B adjusted to 0.1 M NaCl. The enzyme was eluted with a 1500 ml gradient of 0.1 M to 1 M NaCl in buffer B. Fractions were tested for Asc I and exonuclease activity, as described below. The Asc I activity eluted at approximately 62% of the gradient volume. Two hundred mls containing 400,000 units of Asc I activity were pooled and dialysed against buffer C (20 mM KPO4, 0.1 mM EDTA, 6 mM 2-Mercaptoethanol, pH 6.8), adjusted to 0.1 M NaCl. An exonuclease activity eluted at approximately 42% of the gradient volume.

The dialysate was applied to a 59 ml phosphocellulose column equilibrated in buffer C adjusted to 0.1 M NaCl. The column was washed with buffer C. adjusted to 0.1 M NaCl and the Asc I enzyme was eluted with a 600 ml gradient of 0.1 to 1.0 M NaCl in buffer C. The fractions obtained were tested for Asc I and nonspecific endonuclease contamination, as described below. The Asc I activity eluted from 38 to 47% of the gradient volume. An endonuclease contaminant eluted from 44 to 47% of the gradient volume. Asc I activity (180,000 units) from 38 to 43% was pooled and found substantially free of contaminating endonuclease and exonuclease. The Asc I obtained was substantially pure. BSA was added as a stabilizer to give a final concentration of 200 μg/ml and the Asc I was dialysed against storage buffer (50% glycerol, 50 mM NaCl, 20 mM Tris-HCl, 0.1 mM EDTA, 1.0 mM Dithiothreitol, pH 7.5). This final Asc I pool contained 144,000 units, a 36% recovery.

Activity determination

Asc I activity: Samples of from 1 to 10 μls were added to 25 μls of substrate solution consisting of 1× 50 mM potassium acetate, 20 mM Tris-acetate, 10 mM magnesium acetate, 1 mM dithiothreitol (pH 7.9 at 25° C.) containing 0.5 μg Lambda phage DNA. The reaction was incubated at 37° C. for 5 to 60 mins. The reaction was terminated by adding 5 μls of a stop solution (50% glycerol, 50 mM EDTA pH 8.0, and 0.02% Bromophenol Blue). The reaction mixture was applied to a 0.7% agarose gel and electrophoresed. The bands obtained were identified in comparison with DNA size standards.

Exonuclease activity: A 5 μl sample of the protein solution was added to 50 μl of 50 mM potassium acetate, 20 mM Tris-acetate, 10 mM magnesium acetate, 1 mM dithiothreitol (pH 7.9 at 25° C.), containing 25 μg/ml $^3$H-DNA. The reaction was incubated for one hour and the number of TCA soluble and insoluble counts compared. The above sample (25 units) was found to solubilize less than 0.1% of the radioactivity.

Overnight assay for contaminating endonucleases: Twenty-five units of Asc I incubated overnight with lambda DNA showed the same DNA banding pattern on agarose gel assay as one unit of Asc I incubated for one hour with lambda DNA.

Unit Definition: One unit of Asc I is defined as the amount of AscI required to completely cleave 1.0 μg of Lambda DNA in a total reaction volume of 50 μl 50 mM potassium acetate, 20 mM Tris-acetate, 10 mM magnesium acetate, 1 mM dithiothreitol (pH 7.9 at 25° C.) within one hour at 37° C.

Optimal Buffer Conditions: For optimum Asc I activity 50 mM potassium acetate, 20 mM Tris acetate, 10 mM magnesium acetate, 1 mM dithiothreitol (pH 7 9 at 25° C.) was used.

EXAMPLE II

Determination of the AscI Cleavage Site

The location of Asc I cleavage relative to the recognition sequence was determined by two means: standard dideoxy sequencing with cleavage of a primer extension product, and cleavage of an end labeled oligonucleotide.

A. Dideoxy Sequencing Method

As stated above, a ten base oligonucleotide linker containing the Asc I recognition sequence, 5' AGGCGCGCCT 3', was inserted into pUC19 at the Hinc II site to form the plasmid pklAscI-1. This plasmid was then used to determine the AscI cleavage site through the primer extension protocol as follows.

Denaturing the Double-Stranded Template

3 μg of pklASCI-1 cesium purified plasmid (the template) was dissolved in a total of 20 μl dH$_2$O in a 1.5 ml eppendorf tube. 2 μl of 2 M NaOH, 2 mM EDTA was added and the solution incubated 5 minutes at room temperature, following which 7 μl dH$_2$O (4° C.), 7 μl 3 M NaAcetate pH 6.0 (4° C.) and 75 μl Ethanol (4° C.) were added rapidly. The solution was immediately placed in a dry ice/2-propanol bath for 15 minutes to precipitate the DNA. The DNA was pelleted by centrifugation for 10 minutes in an eppendorf centrifuge, 95% of the supernatant was removed by aspiration, 300 μl of 70% ETOH/30% dH$_2$O was added and the solution centrifuged for 5 minutes, followed by removal of approximately 95% of the supernatant. The pellet was then completely dried in a speed vac apparatus for 10 minutes

Sequencing Reactions

To the dried pellet were added 13.5 μl dH$_2$O, 2.25 μl 10× sequencing buffer (75 mM Tris pH 7.6, 55 mM DTT, 50 mM MgCl$_2$), and 1.5 μl of primer (New England Biolabs, Inc. Catalog #1211) solution of 1.0 uM concentration. The solution was incubated at 37° C. for 30 minutes to anneal the primer. 3 μl of [a−35S] dATP at 800 Ci/mmole, 10 mCi/ml was added. 1.5 μl (7.5 units) Klenow fragment DNA polymerase (New England 1 Biolabs, Inc. catalog #210) was added. This solution is called the TPK mixture. 3.2 μl of the TPK mixture was aliquoted into 3 μl of the deoxy/dideoxy nucleotide reaction mixtures (New England Biolabs, Inc. catalog #410) for the A,C,G and T sequencing reactions. The remaining TPK mixture was added to 9 μl of A sequencing reaction mix which contained no dideoxy nucleotides to create a labeled strand of DNA extending through the Asc I recognition site. The reactions were incubated 15 minutes at 37° C. 1 μl of dNTP chase solution (New England Biolabs, Inc. catalog #410) was added to the A,C,G and T reactions and 3 μl chase was added to the extension reaction. The reactions were incubated an additional 15 minutes at 37° C. 6 μl stop solution (New England Biolabs, Inc. catalog #410) was added to the A,C,G and T sequencing reactions and these were stored at −20° C. until run on a sequencing gel. The extension reaction was incubated at 70° C. for 25 minutes to inactivate the DNA polymerase (Klenow), then incubated at room temperature for 10 minutes. 9 μl of the extension reaction was placed in one 0.5 ml eppendorf tube and 6 μl were placed in a second tube. To the 9 μl tube was added 1 μl ( 1 unit) Asc I endonuclease. The reaction was mixed and 2 μl were transferred to the second tube. The enzyme digest reactions were incubated at 37° C. for 30 minutes. Following digestion 4 μl of the reactions were removed and mixed with 5 μl stop solution. To the remaining 4 μl was added 0 25 μl (1.25 units) Klenow fragment and the reaction incubated at room temperature for 12 minutes, after which 5 μl of stop solution was added. The enzyme digest reactions were also stored at −20° C. prior to electrophoresis. The reaction products were electrophoresed on an 8% Bis-Acrylamide sequencing gel, with the AscI digestions of the extension reaction next to the set of sequencing reactions produced from the same primer.

Digestion of the extension reaction product with AscI endonuclease produced a band which co-migrated with the second nucleotide of the AscI recognition sequence GGCGCGCC. Treatment with Klenow fragment following AscI digestion produced a fragment which comigrated with the sixth nucleotide in the AscI recognition sequence GGCGCGCC. These results indicate AscI cleaves DNA between the second and third bases in its recognition sequence 5' GG/CGCGCC 3' to produce a four-base 5' extension.

B. AscI Cleavage Site Determination Using a Synthetic Oligonucleotide

The oligonucleotide AGGCGCGCCT was obtained from New England Biolabs Organic Synthesis Division and labeled at the 5' terminal nucleotide by using $^{32}$P-ATP and T4 polynucleotide kinase (New England Biolabs, catalog #201 as described by manufacturer's literature). This oligonucleotide is self complementary and forms a duplex which contains the recognition sequence for Asc I.

The labeled oligonucleotide was incubated with AscI in the following reaction conditions: 1 μg of the dodecamer was incubated in a 100 μl of buffer (70 mM Tris-HCl (pH 7.6), 10 mM MgCl$_2$, 5 mM DTT), and 5 units of Asc I for 2 hours at 37° C. The reaction was analyzed by DEAE thin layer chromatography (Polygram CEL 300 DEAE-Machery-Nagel) developed in 2% partially hydrolyzed RNA in 7 M urea pH7 at 55° C. d(AG)

(lane b), d(AGG) (lane c), and d(AGGC) (lane d) were $^{32}$P labeled with polynucleotide kinase and used as standards. In a separate reaction BssHII (20 units, New England Biolabs) was also incubated with the labelled dodecamer and this reaction was analyzed as well (lane f). The autoradiogram of the thin layer plate is shown in FIG. 1. Lane a is the unreacted 10 mer, lane g is a mixture of the d(AG), d(AGG) and d(AGGC) oligonucleotides. The mobility of the labeled product of the AscI reaction (lane e) is identical to the 3-mer, d(AGG) (lane c), and the labeled product of the BssHII reaction (lane f) indicating that AscI cleaves DNA between the second and third bases in its recognition sequence 5' GG/CGCGCC 3' to produce a four-base 5' extension. These results are consistent with the dideoxy sequencing reactions in part A of this example.

What is claimed is:

1. A substantially pure Type II restriction endonuclease AscI, which recognizes the following base sequence in double-stranded deoxyribonucleic acid molecules:

and has a cleavage position defined by the arrows.

2. The type II restriction endonuclease of claim 1, cleaving double-stranded deoxyribonucleic acid lambda cI857 and adeno-2 in two positions.

3. A method for obtaining the Type II restriction endonuclease of claim 1, comprising cultivating a sample of Arthrobacter species under conditions favoring the production of said endonuclease and separating said endonuclease therefrom.

4. The type II restriction endonuclease of claim 1, wherein the restriction endonuclease is inactivated by incubation at 65° C. for 25 minutes.

5. The type II restriction endonuclease of claim 1, wherein the restriction endonuclease is purified from Arthrobacter species ATCC#55134.

* * * * *